United States Patent
Phan et al.

(10) Patent No.: US 6,251,312 B1
(45) Date of Patent: Jun. 26, 2001

(54) PRODUCTION METHODS FOR INTRAOCULAR LENSES WITH HIGH PULL STRENGTH FIXATION MEMBERS

(75) Inventors: Quoc Phan, Costa Mesa; Marlene L. Paul, Laguna Niguel, both of CA (US)

(73) Assignee: Allergan, Waco, TX (US)

( * ) Notice: Subject to any disclaimer, the term of this patent is extended or adjusted under 35 U.S.C. 154(b) by 307 days.

(21) Appl. No.: 08/741,070

(22) Filed: Oct. 30, 1996

(51) Int. Cl.[7] ............................. B29D 11/00; A61F 2/16
(52) U.S. Cl. ..................... 264/1.7; 623/6.46; 623/901
(58) Field of Search ..................... 623/6, 901, 6.46, 623/6.59; 264/1.7, 1.26, 2.6

(56) References Cited

U.S. PATENT DOCUMENTS

| | | |
|---|---|---|
| 4,668,446 | 5/1987 | Kaplan et al. . |
| 4,786,445 * | 11/1988 | Portnoy et al. ................. 264/1.4 |
| 4,790,846 | 12/1988 | Christ et al. . |
| 4,834,749 * | 5/1989 | Orlosky ......................... 623/6 |
| 5,147,397 | 9/1992 | Christ et al. . |
| 5,185,107 | 2/1993 | Blake . |
| 5,252,262 * | 10/1993 | Patel ............................. 264/1.4 |
| 5,423,929 | 6/1995 | Doyle et al. . |
| 5,523,029 * | 6/1996 | Korgel et al. ................ 264/1.37 |

* cited by examiner

Primary Examiner—Paul B. Prebilic
(74) Attorney, Agent, or Firm—Stout, Uxa, Buyan, & Mullins, LLP; Frank J. Uxa

(57) ABSTRACT

New methods for producing intraocular lenses (IOLs) include a combination of steps which provide outstanding pull strength between the fixation member of the IOL and the optic of the IOL without requiring the lens body region of the fixation member to have enlarged anchor structures. In one embodiment, the present methods include providing an optic member having a recess; providing a fixation member having a lens bonding region free of enlarged anchor structures; placing the lens bonding region into the recess; and thereafter doing at least one of reducing the size of the recess and increasing the cross-sectional area of the lens bonding region. The lens bonding region of the fixation member is thereby secured to the optic member.

19 Claims, 1 Drawing Sheet

PRODUCTION METHODS FOR INTRAOCULAR LENSES WITH HIGH PULL STRENGTH FIXATION MEMBERS

BACKGROUND OF THE INVENTION

This invention relates to intraocular lenses (IOLs) and to methods for producing IOLs. More particularly, the present invention relates to very straight forward and easy to practice methods for producing IOLs with optics comprising polymeric materials, for example, silicone polymeric materials. IOLs produced in accordance with the present invention have advantageous properties, for example, outstanding fixation member pull strengths, that is advantageously large bond strengths between the optic of the IOL and the fixation member or members of the IOL.

The use of IOLs to improve vision and/or to replace damaged or diseased natural lenses in human eyes, particularly natural lenses impaired by cataracts, has achieved wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, for contacting eye tissue to fix or hold the IOL in the proper position after implantation. The optic may comprise a soft, resilient material, such as a silicone polymeric material (in particular, an elastomeric cross-linked silicone polymeric material), an acrylic material and the like. The haptics typically comprise a filament constructed of a resilient metal or polymeric substance, such as polymethylmethacrylate (PMMA), polyamide, polypropylene and the like.

Each of the filament haptics is preferably flexible to reduce trauma to sensitive eye structures and to be yielding during insertion of the IOL. In addition, filament haptics generally have a memory retaining capability, e.g., springiness, so that after implantation of an associated IOL, the filament haptics automatically tend to return to their normal orientation.

Although the filament haptics are very useful, certain difficulties remain. For example, filament haptics and soft or deformable optics tend to be formed from dissimilar materials which do not ordinarily chemically bond together. As a result, filament haptics have been designed having a variety of enlarged attachment end configurations or structures, e.g., anchor structures, for providing a physical or mechanical interlock between the haptic and optic. Polypropylene haptics, for example, have been secured into silicone polymer-based optics by means of a mechanical lock. This lock may comprise a small loop or other anchor formed at the attachment end or lens bonding region of the haptic, which is then placed in a mold. The precursor material of the silicone polymer-based optic is poured into the mold, through and/or around the lens bonding region of the included haptic or haptics, and is then cured. Christ et al U.S. Pat. No. 4,790,846 discloses the molding of an optic around a haptic having a small loop or other anchor to effect a secure haptic connection.

Christ et al U.S. Pat. No. 4,790,846 further discloses a method for making an IOL in which a region of an elongated filament haptic has a different configuration, e.g., a bulbous enlargement, which cooperates with the optic of the IOL to form a mechanical interlock between this different configuration and the optic. If desired, the bulbous enlargement may have its outer surface roughened to improve adhesion of the material of the optic.

Kaplan et al U.S. Pat. No. 4,668,446 discloses securing a haptic having an enlarged portion to an IOL by swelling the lens material having a drilled peripheral bore with an organic liquid or vapor. After the enlarged portion of the haptic is inserted into the peripheral bore of the lens, the organic fluid is removed.

In general, the use of enlarged attachments, configurations and portions makes it more difficult, complex and time-consuming to produce IOLs. For example, such enlargements must be produced or formed on the haptic before the haptic is attached to the optic. This additional step is costly and time-consuming. It would be advantageous to obtain effective haptic/optic securement and pull strength without the need for such enlarged attachments, configurations and portions.

Blake et al U.S. Pat. No. 5,104,590 discloses improving the adhesive properties of polypropylene haptics to silicone lenses through surface treatment of the haptic with a combination of a high frequency corona discharge and a silicone primer. Christ et al U.S. Pat. No. 5,147,397 discloses exposing the lens bonding region of the haptic to a plasma at conditions effective to enhance the bondability of the lens bonding region to the optic. While these procedures can be effective in enhancing haptic/optic bond strength, they are relatively sophisticated and are relatively expensive to practice, thus adding to the complexity and cost of producing IOLs. In addition, substantial care must be exercised in controlling the corona discharge and plasma exposing procedures to avoid damaging the relatively fine filament haptics.

Doyle et al U.S. Pat. No. 5,423,929 discloses bonding a fixation member to an optic of an IOL using a primer component coated on the fixation member. Using this system, good fixation member optic bond strengths are obtained. However, these methods do involve a step of placing a primer component on the fixation member. Also, the presence of the primer component or a residue thereof in the eye (with the final IOL) may have some potential impact on the IOL patient.

It would be advantageous to provide a more straight forward and easy to practice method of producing IOLs which effectively enhances the bond or pull strength between the fixation member or members and the optic.

SUMMARY OF THE INVENTION

New methods for producing IOLs have been discovered. The present production methods are very straight forward, easy to practice and cost effective, and provide IOLs which have outstanding fixation member pull strengths. Further, this high or large pull strength is achieved with little or no risk of detrimentally affecting the intrinsic strength and other advantageous properties of the fixation member in producing the IOL. It has been found that acceptably large fixation member pull strengths are achieved preferably using fixation members with lens bonding regions which are free of enlarged anchor structures, and preferably without requiring activation of the fixation member surface with high frequency corona discharge or plasma and without coating the fixation member surface with primer component. The present methods very reliably, predictably and reproducible produce high quality IOLs.

In addition, since in accordance with the present invention the optic is formed prior to joining the fixation member or members to the optic, the conditions at which the optic is formed can be chosen to optimize the properties of the optic without consideration for possible damage to the relatively fine filament haptic. Also, relatively low melting point materials of construction can be used in the fixation members. Moreover, the cost of the IOL is reduced, for example, because simplified optic molding or other optic forming procedures can be employed. Increased flexibility in molding cycle time and curing temperature, and increased interchangeability in the mold tooling required for optic forming results because the fixation member is not present when the optic is being formed. This increased flexibility and interchangeability, in turn, increase production capacity and/or reduce capital and product development costs.

In one broad aspect, the present invention is directed to methods for producing an IOL including an optic and at least one fixation member having a proximal end or lens bonding region located in the optic. In this aspect, the present methods comprise providing an optic member having a recess; providing a fixation member having a lens bonding region, preferably free of enlarged anchor structures; placing the lens bonding region of the fixation member into the recess; and thereafter doing at least one of reducing the size of the recess and increasing the cross-sectional area of the lens bonding region, thereby securing the lens bonding region of the fixation member to the optic member. In one useful embodiment, the recess is enlarged and/or the cross-section of the lens bonding region is decreased prior to the lens bonding region being placed in the recess. The lens bonding region of the fixation member, and preferably the entire fixation member, is preferably subjected to no high frequency corona discharge or plasma activation or other exotic activation procedure, and has no primer component coating.

In one particularly useful embodiment, the present methods comprise providing an optic member comprising a polymeric material, preferably a cross-linked polymeric material, having a recess; providing a fixation member having a lens bonding region, preferably free of enlarged anchor structures; contacting the optic member with an organic fluid to enlarge the optic member; thereafter placing the lens bonding region of the fixation member into the recess; and, thereafter reducing the size of the recess including removing the organic fluid from the optic member, thereby securing the lens bonding region of the fixation member to the optic member. The recess can be formed in the optic member before or after the optic member is enlarged. The organic fluid is selected to be effective to enlarge the optic member. The organic fluid may also be effective to remove, for example, extract, unwanted materials, such as unreacted oligomers, from the optic member. This optional removal or extraction feature is within the scope of the present invention.

The present methods facilitate the production of IOLs having very consistent haptic/optic pull strengths of at least 40 grams, more preferably of at least the current ANSI standard of 50 grams minimum, and still more preferably of at least 60 grams.

The invention, together with additional features and advantages thereof may best be understood by reference to the following description taken in connection with the accompanying illustrative drawings.

DETAILED DESCRIPTION OF THE INVENTION

Figure 1:
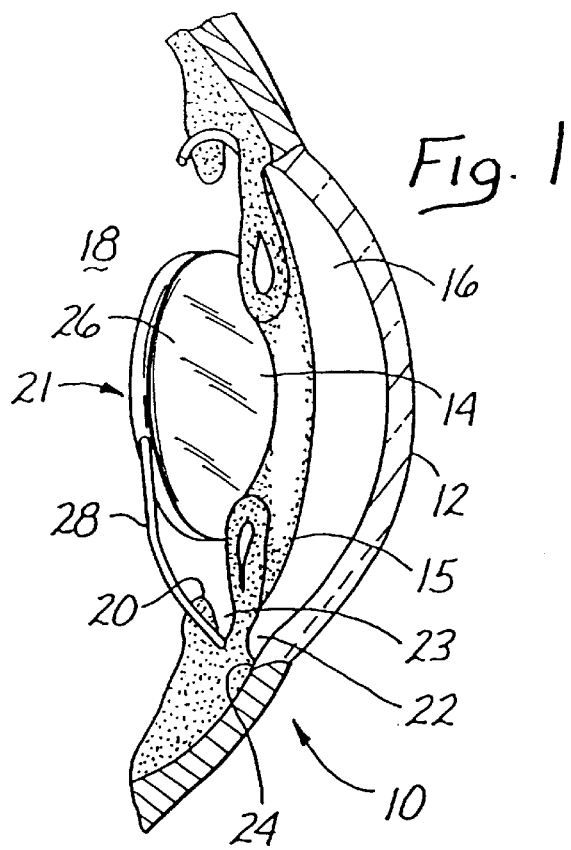
FIG. 1 is a simplified representation of the physiology of the human eye.

The present invention is based, in part, upon the discovery that the fixation member or members of an IOL can be attached or secured to the optic of the IOL with acceptably high pull strength without requiring enlarged anchor structures, and preferably without modification to or coating of the surface of the fixation member or members. In particular, satisfactory pull strengths of fixation member or members relative to the optic of an IOL are obtained preferably without the fixation member being subjected to high frequency corona discharge activation or plasma activation and without the fixation member being coated with a primer material. Because no such surface activation or coating is required, the risk that such activation procedure or coating will affect the structure and other advantageous properties of the fixation member or members can be eliminated.

The present methods produce IOLs including an optic, which has an optical zone through which light passes so that the IOL patient has improved vision, and at least one fixation member, preferably two fixation members, having a proximal end portion or lens bonding region located in the optic.

The present methods provide for attaching a fixation member to the optic of an IOL. In general, the present methods comprise providing an optic member having a recess, and providing a fixation member having a lens bonding region, preferably free of enlarged anchor structures. The lens bonding region of the fixation member is placed into the recess. After this has been accomplished, at least one of the following is done: reducing the size of the recess and increasing the cross-sectional area of the lens bonding region, thereby securing the lens bonding region of the fixation member to the optic member. The optic member and/or recess may be enlarged and/or the cross-sectional area of the lens bonding region may be decreased before the lens bonding region is placed in the recess. The lens bonding region is secured to the optic member with a pull strength of at least 40 grams, more preferably at least 50 grams and still more preferably at least 60 grams.

The optic member may be temporarily and non-destructively enlarged or deformed by using an organic fluid which temporarily and non-destructively swells the optic member and/or by temporarily and non-destructively heating the optic member and/or by temporarily and non-destructively stretching the optic member. The size or cross-section of the fixation member can be temporarily and non-destructively decreased or reduced, for example, by stretching and/or cooling. The fixation member is easily placed into the recess which has been temporarily increased in size or when the lens bonding region of the fixation member has been temporarily decreased in size. Once the lens bonding region of the fixation member is in the recess of the optic member, the optic member and/or fixation member are then returned to normal or original size or dimensions. The fixation member is held in the recess of the optic member, that is secured to the optic member, by pressure/force caused at the fixation member/optic member interface as the optic member and/or fixation member return to normal or original size or dimensions.

Although many combinations of steps are suitable, the present methods preferably include enlarging the optic member and recess and, thereafter, reducing the size of the recess with the lens bonding region located therein.

More preferably, the optic member comprises a material swellable by an organic fluid, that is an organic liquid or vapor, and the enlarging step comprises swelling the optic member with the organic fluid. In this embodiment, the reducing step preferably comprises removing the organic fluid from the optic member. This reducing step preferably includes subjecting the optic member to conditions, for example, ambient temperature or an elevated temperature for a sufficient time, effective to evaporate the organic fluid from the optic member. Such conditions can be considered to be preferably effective to dry the optic member free of the organic fluid.

Any suitable method for swelling the optic member with the organic fluid may be employed. In general, the optic member is contacted with the organic fluid at conditions effective to swell the optic member. This contacting may, for example, include one or more of the following: immersing and/or dipping the optic member in the organic fluid, spraying the optic member with the organic fluid, exposing the optic member to a gaseous medium including the organic fluid (in vapor form) and the like.

The conditions at which such contacting occurs can vary over a wide range and are dependent on various factors, for example, the material of construction and size of the optic member, the specific organic fluid being employed, the specific mode of contacting being employed and the like factors. Of course, the conditions should be effective to swell the optic member by the desired degree while having no undue permanent detrimental effect on the optic member. The temperatures chosen should be such that the fluid state of the organic fluid is maintained. Temperatures in the range of about 0° C. to about 60° C. or about 100° C. are often useful, with ambient temperature (18° C.–25° C.) being convenient and effective in most cases. Contacting times may range from about 1 second to about 1 minute or about 5 minutes or more.

Although a primary purpose of the organic fluid is to enlarge or swell the optic member, such fluid may also be effective in removing, e.g., extracting, unwanted materials, such as unreacted oligomers, from the optic member. Such removal of unwanted materials enhances one or more properties, for example, optical properties, of the optic member and/or ultimately reduces the risk of placing these unwanted materials in the eye, with the final IOL product. The use of an organic fluid to both enlarge the optic member and remove unwanted material from the optic member is included within the scope of the present invention.

Following insertion of the fixation member into the recess of the swollen optic member, the organic fluid is removed. This removal, preferably at ambient temperature or elevated temperature, may be done, for example, open to the atmosphere or in an oven and for a time sufficient to remove organic fluid from the optic member so that it returns to approximately or substantially its original size. In so doing, the fixation member is secured to the optic member.

Although any suitable processing step or steps may be employed to remove the organic fluid from the swelled optic member, it is preferred that such removing comprise subjecting the swelled optic member to air (or other gaseous medium substantially free of the organic fluid) for a time sufficient to remove at least about 50%, more preferably at least about 70% and still more preferably at least about 90%, of the organic fluid from the optic member. Substantially all of the organic fluid is preferably removed from the optic member.

The conditions for removing organic fluid from the swelled optic member should, of course, be effective and should have no undue detrimental effect on the optic member or the fixation member or members located in the recess or recesses. The specific conditions chosen can vary widely depending, for example, on the material of construction and size of the optic member, on the specific organic fluid being used, on the specific amount of organic fluid to be removed from the optic member and the like factors.

Temperatures in the range of about 0° C. to about 110° C. or about 125° C. are often effective. Ambient temperature is very convenient and useful. The swelled optics may be maintained at such temperatures for periods of time in the range of about 30 seconds or about 1 minute to about 5 minutes or about 30 minutes or longer.

Preferably, at least a portion of the organic fluid is introduced into the optic member to effect the swelling. For example, the organic fluid may be absorbed into the optic member. As noted above, this swelling is temporary and, therefore, it is preferred that no chemical reaction between the organic fluid and the optic member occurs.

The conditions at which the optic member is swelled are to some extent related. For example, the higher the temperature of the organic fluid the shorter the time to swell the optic member. Similarly, the higher the temperatures used to remove the organic fluid the shorter the turn needed to remove the fluid from the optic member. In any event, such conditions should be chosen to avoid undue permanent damage to the optic member, fixation member or members and the wearer of the IOL.

In certain circumstances, it is important to place the lens bonding region of the fixation member in the recess promptly, or even immediately, for example, within about 1 minute or within about 5 minutes, after the optic member has been swelled. Once the optic member has been removed from swelling conditions, it quickly starts to return to normal size, if the fixation member or members are not promptly placed in the recess of recesses, the optic member will become smaller and it will become impossible to fit the fixation member or members in the recess or recesses.

Any suitable organic fluid may be employed. Such fluid should have no undue permanent detrimental effect on the optic member, fixation member or members, IOL or the patient in whose eye the IOL in implanted. The specific organic fluid used depends, for example, on the specific materials from which the optic member and fixation member or members are made. Particularly useful organic fluids comprise materials selected from hydrocarbons, preferably having up to about 30 carbon atoms per molecule; alcohols, preferably having 1 to about 10 carbon atoms per molecule; substituted alcohols; oxygenated hydrocarbons, such as ethers, ketones and aldehydes, preferably having 1 to about 10 carbon atoms per molecule; substituted oxygenated hydrocarbons and the like and mixtures thereof. Particularly useful are aliphatic hydrocarbons, such as alkanes having about 3 to about 10 or more carbon atoms per molecule; alcohols, such as alkanols having 1 to about 3 or about 6 to about 8 carbon atoms per molecule; alkyl ethers having about 2 to about 10 carbon atoms per molecule and mixtures thereof.

The optic members useful in the present invention may comprise materials, preferably polymeric materials, such as hydrogel-forming polymers, polyphosphazenes, polyurethanes, polyacrylates, silicone polymers, and the like and mixtures thereof, e.g., such as are known in the art. The present invention is particularly advantageous when the optic member is constructed of soft, resilient, deformable materials, preferably including cross-linked polymeric materials. Rigid optic materials, such as polycarbonates, polysulphones and PMMA, may also be used provided that such materials can be temporarily non-destructively swelled. In all cases, the particular material chosen should produce an optically clear optic and exhibit biocompatibility in the environment of the eye. Selection parameters for suitable IOL materials are well known to one of skill in the art.

In one particularly useful embodiment, the optic member comprises a silicone polymeric material, for example, an elastomeric, cross-linked silicone polymeric material. Such optic may be, and preferably is, derived from a two part silicone formulation which is introduced into a mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes. In one particularly useful embodiment, the optic comprises a polymer which is a platinum-catalyzed, vinyl/hydride, addition cured polyorganosiloxane. One particularly useful optic composition includes a silicone polymeric material which is reinforced, for example, with an effective reinforcing amount of a suitable resin and/or silica. The present optics may include one or more other components in amounts effective to provide a beneficial property to the optic. For example, an effective amount of an ultraviolet light absorbing component may be included, preferably covalently bonded to the silicone polymeric material of the optic.

The present methods may include forming an optic member. Although other suitable techniques may be employed to form the optic member, one particularly useful approach is to form a precursor composition and inject such precursor composition into a suitable mold. The precursor-containing mold is then subjected to effective conditions, for example, conventional silicone curing conditions, to cure the precursor composition into the desired silicone polymeric material. The cured material is then removed from the mold and is ready for additional processing in accordance with the present invention. Of course, preformed optic members can be provided from other sources and, therefore, the optic member forming need not be part of the present methods.

The optic member is preferably formed with no recess or recesses for insertion of the fixation member or members. This feature, in which the optic member as formed includes no recess or recesses for the fixation member or members, greatly simplifies the procedure by which the optic member is formed. For example, in the molding approach, the mold does not have any additional wires or other means by which recesses for the fixation members are incorporated into the formed optic member. Also, since no such recesses are formed and the fixation member or members are not included during the optic member forming step, there is no concern with the fixation member or members at this point in the method. Thus, there is more flexibility in the mold cycle time and curing temperature, and more interchangeability in the mold tooling. This, in turn, increases production capacity and reduces capital, operating and other costs. Also, since the fixation member or members are not exposed to prolonged curing conditions, a wider variety of fixation member materials of construction, for example, including low melting materials or construction, can be employed.

In one embodiment, a recess forming step is included and comprises puncturing the optic member, for example, with a needle-like implement which is then removed from the optic member. The recess forming step can be conducted either before or after the optic member enlarging step. The recess forming step is preferably conducted, for example, with the needle-like implement noted above, without removing material from the optic member. This preferred feature of the present invention is in contrast to Kaplan U.S. Pat. No. 4,668,446 which discloses drilling the lens to form a peripheral bore. Such drilling results in removing lens material to form the bore. Forming the recess without removing material from the optic member, as preferred in the present invention, results in generally higher optic/fixation member pull strengths, for example, because the optic member includes more material applying force or pressure to hold the fixation member in place in the recess.

Each fixation member typically comprises a flexible member comprising metal or, preferably, polymeric material, and has a substantially circular cross-section, although alternate cross-sectional configurations may be substituted, if desired. The lens bonding region of the fixation member is free of enlarged anchor structures. The cross-sectional area of the present fixation members is preferably substantially uniform along the length of the fixation member or members. The fixation members have sufficient strength to provide support for the IOL in the eye. The fixation members may comprise any variety of materials which exhibit sufficient supporting strength and resilience and which are substantially biologically inert in the intended in vivo environment. Suitable materials for this purpose include, for example, polymeric materials such as polypropylene, PMMA, polycarbonates, polyamides, polyimides, polyacrylates, polyhydroxyethylmethacrylate, poly (vinylidine fluoride), polytetrafluoroethylene and the like, and metals such as stainless steel, platinum, titanium, tantalum, shape-memory alloys, e.g., nitonal, and the like. More preferably the fixation member or members comprise a polymeric material, such as those selected from polypropylene, PMMA and polyimides, especially extruded PMMA and polypropylene. The fixation members can be produced using conventional and well known forming techniques. For example, the preferred polymeric fixation members can be formed in accordance with known thermoplastic polymer forming techniques, such as by injection molding or by extrusion.

As noted above, the formed optic member preferably does not include any recess or recesses into which the fixation member or members can be placed. In this circumstance, a recess or recesses are separately formed in the pre-formed or already formed optic member, for example, before or after the optic member is enlarged. Such recess or recesses, based on a normally sized optic member, may have cross-sections which range from more than to less than the cross-sections of the normally sized fixation member or members. Although such recesses preferably have cross-sections which are about equal to or less than the cross-sections of such fixation members, the recesses can have larger cross sections, for example, up to about 20% larger, than the cross-sections of the fixation members. This is particularly true when, as is preferred, the recesses are formed without removing any of the optic member.

Particularly useful silicone polymeric materials for use as optic member materials of construction are reinforced elastomeric compositions including polysiloxane elastomers, preferably having the chemical composition of a cross-linked copolymer including about 12 to about 18 mol percent of aryl substituted siloxane units of the formula $R_4R_5$—SiO where the aryl substituents ($R_4$ and $R_5$ groups) can be independently selected from phenyl groups, mono-lower alkyl substituted phenyl groups, and di-lower alkyl substituted phenyl groups. Preferably, both aryl groups are simple phenyl, and the resulting diphenyl siloxane unit is present in the copolymer in an amount of about 14 to about 18 mole percent. Very useful optic member materials of construction include those disclosed in Doyle et al U.S. Pat. No. 5,423,929, the disclosure of which is hereby incorporated in its entirety herein by reference.

Referring now to FIG. 1, there is depicted in vivo placement into an eye 10 of an IOL 21 according to the present invention, in which the optic member was formed, recesses formed, swelling, insertion of fixation members and removal of organic fluid.

The cornea 12 serves as a refractory medium in addition to its function as the anterior wall of the eye 10. The pupil 14 and the iris 15 of variable aperture are located behind the cornea 12 and divide the eye into an anterior chamber 16 and a posterior chamber 18. The natural crystalline lens (not illustrated) is connected by zonular fibers to a peripheral muscle about the lens known as the ciliary muscle 20.

The surgical implantation of IOL 21 is accomplished by an incision in the eye, removal of the diseased or damaged natural lens (if applicable) and insertion of the IOL into the eye. The optic 26 of IOL 21 includes a centrally located optical zone and may be configured for implantation into a specific one or either of the anterior or posterior chambers 16 or 18. The haptics 28 of IOL 21 extend radially outwardly in the general plane of the optic 26.

A peripheral limit of anterior chamber angle 22 exists between the base of the iris 15 and a scleral spur, which serves as a support location for IOL 21 implanted within the anterior chamber 16 of the eye 10. A peripheral zone 23 also exists within the posterior chamber 18 between the ciliary muscle 20 and the base of the iris 15, which is known as the ciliary sulcus 24. The peripheral zone 23 serves as a mountain location for IOL 21 within the posterior chamber 18. Referring to FIG. 1, IOL 21 is shown positioned in the posterior chamber 18 and is supported by the haptics 28 bearing upon the ciliary sulcus 24.

Figure 2:
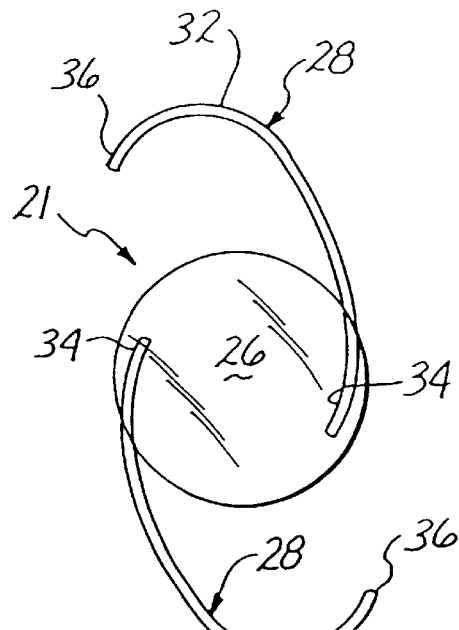
FIG. 2 is a plan view of an IOL produced in accordance with the present invention.
Figure 3:
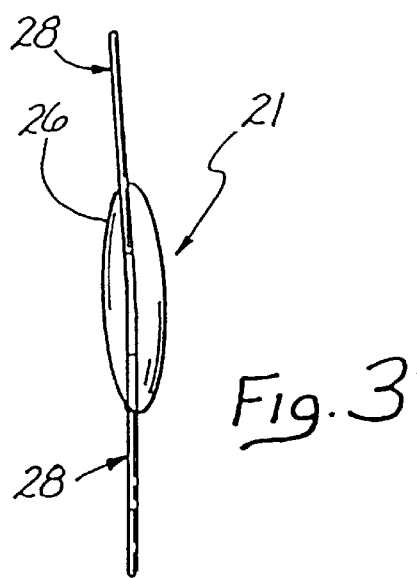
FIG. 3 is a side view of the IOL of FIG. 2.

Referring now to FIGS. 2 and 3, IOL 21 is illustrated as including a pair of radially outwardly extending haptics 28 secured to optic 26. The optic 26 is made of an optically clear, silica reinforced, platinum-catalyzed, vinyl/hydride addition cured (cross-linked) polyorganosiloxane polymer and has a index of refraction (refractive index) of about 1.46. Each haptic 28 has a substantially uniform cross sectional area throughout its length and is shown provided with a smoothly curved region 32, intermediate a lens bonding region 34 and a free end region 36. Although the illustrated embodiment is provided with two opposing haptics 28, it is understood that an IOL having only haptic or more than two haptics bonded to the optic by the method disclosed herein is considered within the scope of the invention.

IOL 21 is produced in accordance with the present invention, as described herein. Briefly, the optic 26 is formed, with no recesses to accommodate the haptics 28, by conventional molding techniques from a cross-linked silicone polymeric material. If desired, the lens bonding regions 34 of haptics 28 can be mechanically roughened, for example, by abrasion techniques and the like, to facilitate further increased haptic/optic bond strengths. Recesses are formed in formed optic 26 to accommodate the lens bonding regions 34 of haptics 28. Such recesses may be formed, for example, by puncturing optic 26 to an appropriate depth and at an appropriate location with a needle or a machine tool, such as a drill and the like, or by using photo ablation, ultrasound or a water jet.

Each of the recesses is formed, preferably without removing any portion of the optic member, such as with a needle-like implement, having a size smaller than or equal to that needed to accommodate a lens bonding region 34. The optic member is immersed in heptane at ambient temperature for 10 seconds to swell the optic member and enlarge the recess. The lens bonding region of the fixation member is inserted in the enlarged recess. The enlarged optic member/fixation member assembly is then maintained in air at ambient temperature for about 1 to about 10 minutes to remove the heptane.

The assembled optic 26/haptics 28, which has no primer component or residue thereof between the optic and the lens bonding regions 34 and has outstanding haptic/optic pull strength, may be further processed, for example, using one or more conventional lens finishing techniques, and then packaged ready for shipment. IOL 26 may be implanted in the eye 10 using conventional techniques. After implantation, IOL 21 functions very effectively.

The present methods are very straightforward, easy and inexpensive to practice, and are effective in providing IOLs which have outstanding fixation member/optic pull strengths. Moreover, no exotic activation procedures and no primer coatings are necessary to prepare the fixation members for use in the present IOLs.

The following non-limiting example illustrates certain aspects of the present invention.

EXAMPLE

A series of 22 IOL optics were selected for testing.

Each of the optics had the same chemical composition, a silica reinforced, platinum-catalyzed, vinyl/hydride addition-cured cross-linked) polyorganosiloxane polymer. A vinyl functional benzotriazole was covalently bonded into this polymer to provide for ultraviolet light absorbance. The index of refraction of these optics was about 1.46. The optics each had a configuration to the optic of the IOL sold by Allergan, Inc. under the trademark SI-40NB.

Filament haptics, made of polymethylmethacrylate were provided. Each of these haptics was constructed with no anchor structures and had a substantially uniform cross-sectional area along its length. The outer diameters of the haptics were 0.006 inch. None of the haptics were subjected to high frequency corona discharge activation or plasma activation or were coated with primer.

The optics were produced, that is molded, with no recesses. Using a needle having a 0.005 inch diameter, two recesses were formed in each optic to a nominal depth of 0.061 inch without removing any material from the optics.

Each of the optics were immersed in liquid heptane at ambient temperature for about 10 seconds which caused the optic to swell. The recesses in the swollen optics were also enlarged sufficiently to allow the easy introduction of a haptic into each recess. After the optic was removed from the heptane, the haptics were promptly placed in the enlarged recesses. After the haptics had been placed in the enlarged recesses, the optic/haptic assemblies were maintained in air at ambient temperature for about 3 to 5 minutes to remove the heptane from the optics. This resulted in the optics returning to their original size and the haptics becoming secured to the optics.

Afterwards, the optic/haptic pull strength was tested as follows. Using a Chatillon Model LTCM tensile tester, the haptics were pulled from each of the optics and the pull force (in grams) required to achieve this separation was recorded. In addition, the insertion depth of each haptic was measured and recorded.

For the 22 IOL optics tested, the insertion depth of the haptics ranged from 0.0582 inch to 0.0667 inch, and the pull strength ranged from 53 grams to 82 grams. The average pull strength was 67.3 grams with a standard deviation of 7.3.

These results demonstrate that outstanding optic/haptic pull strengths are achieved in accordance with the present invention. For example, in each of the tests reported above, the optic/haptic pull strength exceeded the current ANSI standard of 50 grams minimum. This is particularly surprising since the lens bonding region of each of the haptics included no enlarged anchor structures, was subjected to no exotic activation procedure and was not coated with any primer. In addition, the relatively low standard deviation reported above indicates that the present methods provide controlled and reproducible results, which feature is important in producing IOLs with consistent properties.

While this invention has been described with respect to various specific examples and embodiments, it is to be understood that the invention is not limited thereto and that it can be variously practiced within the scope of the following claims.

What is claimed is:

1. A method for attaching a fixation member to the optic of an intraocular lens which comprises:

providing an optic member having a recess;

providing a fixation member having a lens bonding region free of enlarged anchor structures;

placing the lens bonding region free of enlarged anchor structures into said recess; and thereafter securing said lens bonding region free of enlarged anchor structures to said optic member by reducing the size of said recess.

2. The method of claim 1 wherein said lens bonding region is secured to said optic member with a pull strength of at least 50 grams.

3. The method of claim 1 wherein said lens bonding region is secured to said optic member with a pull strength of at least 60 grams.

4. The method of claim 1 wherein said providing an optic member step includes forming said recess in said optic member without removing any of said optic member.

5. The method of claim 1 which further comprises enlarging said optic member prior to said placing step.

6. The method of claim 5 wherein said providing an optic member step includes forming said recess in said optic member after said enlarging step.

7. The method of claim 5 wherein said providing an optic member step includes forming said recess in said optic member without removing any of said optic member.

8. The method of claim 5 wherein said optic member comprises a material swellable by an organic fluid and said enlarging step comprises swelling said optic member with said organic fluid.

9. The method of claim 8 wherein said reducing step comprises removing said organic fluid from said optic member.

10. The method of claim 1 wherein said optic member comprises a polymeric material.

11. The method of claim 8 wherein said optic member comprises a cross-linked polymeric material.

12. The method of claim 1 wherein said fixation member comprises a polymeric material.

13. The method of claim 8 wherein said organic liquid comprises a material selected from the group consisting of hydrocarbons having up to about 30 carbon atoms per molecule, alcohols having 1 to about 10 carbons atoms per molecule, oxygenated hydrocarbons having 1 to about 10 carbon atoms per molecule and mixtures thereof.

14. A method for attaching a fixation member to the optic of an intraocular lens which comprises:

providing an optic member comprising a cross-linked polymeric material, said optic member having a recess;

providing a fixation member having a lens bonding region free of enlarged anchor structures;

contacting said optic member with an organic fluid to enlarge said optic member; thereafter placing the lens bonding region free of enlarged anchor structures into said recess; and, thereafter securing said lens bonding region free of enlarged anchor structures to said optic member by reducing the size of said recess including removing said organic fluid from said optic member.

15. The method of claim 14 wherein said lens bonding region is secured to said optic member with a pull strength of at least 50 grams.

16. The method of claim 14 wherein said optic member comprises a cross-linked silicone polymeric material, and said fixation member comprises a polymeric material.

17. The method of claim 14 wherein said providing an optic member step includes forming said recess in said optic member without removing any of said optic member.

18. The method of claim 14 wherein said providing an optic member step includes forming said recess in said optic member after said contacting step.

19. The method of claim 14 wherein said organic liquid comprises a material selected from the group consisting of hydrocarbons having up to about 30 carbon atoms per molecule, alcohols having 1 to about 10 carbons atoms per molecule, oxygenated hydrocarbons having 1 to about 10 carbon atoms per molecule and mixtures thereof.

* * * * *